United States Patent [19]

Gupta et al.

[11] Patent Number: 5,847,209
[45] Date of Patent: Dec. 8, 1998

[54] PROCESS FOR RECOVERY OF SOLID AND REUSABLE UREA FROM THE UREA ADDUCTION PROCESS

[76] Inventors: Anurag Ateet Gupta, 1781 Sector 9; Krishan Kumar Swamy, 494 Sector 7B, both of Faridabad-121006; Shanti Prakash, 605 Sector 7, Urban Estate, Gurgaon-122001; Madan Mohan Rai, 886 Sector 15, Faridabad-121007; Akhilesh Kumar Bhatnagar, 205 Sector 7A, Faridabad-121006, all of India

[21] Appl. No.: 984,209

[22] Filed: Dec. 3, 1997

[51] Int. Cl.$^6$ .................................................. C07C 273/16
[52] U.S. Cl. ................. 564/73; 564/1.5; 564/63; 208/24; 208/289; 196/14.5
[58] Field of Search .................................. 564/1.5, 63, 73; 208/24, 289; 196/14.5

[56] References Cited

U.S. PATENT DOCUMENTS 2,619,501  11/1952  Ray ........................................... 564/73

*Primary Examiner*—Peter O'Sullivan
*Attorney, Agent, or Firm*—Spencer & Frank

[57] ABSTRACT

A process for recovery of solid and reusable urea from the urea adduction process. Refinery streams are subjected to a step of urea adduction for removal of unwanted branched products, aromatics and sulphur. The adduct is purified, dried and then subjected to the step of mechanical shearing.

8 Claims, No Drawings

PROCESS FOR RECOVERY OF SOLID AND REUSABLE UREA FROM THE UREA ADDUCTION PROCESS

FIELD OF INVENTION

This invention relates to a novel process for the isolation of solid and reusable urea from the urea adduction process.

PRIOR ART

Alpha olefins and normal paraffins are isolated from petroleum streams using one of the following processes:

(i) Adsorption & desorption
(ii) Extraction
(iii) Urea adduction or dewaxing

However, the inclusion compounds of urea are the most widely studied and extensively investigated. This could be partly due to the result of their applicability in the field of petroleum and petrochemical industry.

Bengen's discovery in 1940 (F.Bengen, German Patent Application OZ 12438, Mar. 18, 1940) of addition complexes formed between urea and various straight chain organic compounds was kept secret by Germany during the Second World War. After the war, it appeared on a microfilm of Technical Oil Mission (Technical Oil Mission, Reel 143, pp 135-9, Robert & Weadman, "advances in Pet.Chem. & Refining", Vol. 1, Ed.Kobe-Mc Ketta, Interscience, Newyork, 1964) and aroused widespread interest. Since then the mechanism of adduction has been subject of various studies (Daniel Swern, Ind.Eng.Chem.,47,216,1955; L. C. Fetterly, Pet. Refiner, 36 (7), 145,1957) and the method has found its application in the separation of straight chain compounds. A number of reviews have been published by Mc Laughlin (Mc Laughlin, R. L., in B. T. Brooks et al., Eds "The Chemistry of Petroleum Hydrocarbons", Vol.1, Reinhold, Newyork, 1954, pp 241–273), Fatterly (Fetterly, L. C., Petrol, Refiner, 36 (7), 145–152, 1957), W.Schlenk, Jr. (Schlenk, Jr.,W., Forschr, Chem.Forsch.2, 92–145, 1951) and kobe and Domask (Kobe, K. A. and W. G. Domask, Petrol Ref. 31 (3), 106–113; No.5, 151–157; No. 7, 125–129, 1952).

Basically the urea adduction process involves four stages;

(i) Adduct Formation
(ii) Separation
(iii) Decomposition
(iv) Finishing step

Based on the physical state of the urea used, following are the commercial applications of urea adduction in petroleum industry.

(a) Sonneborn's Petrolia Refinery, Pennsylvania; (Ref: A. Hoppe "advances in Pet. Chem. and Refining", Vol. 8, Ed. Kobe-Mcketta, Interscience Pub, Newyouk, 1964; C. S. Croman, Chem. Eng., 66, 142, 1959; A. Hoppe and H.Franz, Pet.Refiner, 36(5), 221, 1957).

In operation since 1950, it is said to be the first commercial unit applying urea dewaxing. It is designed to improve the cloud point and pour point of medicinal white oils. It is a solid urea process. The adduct decomposition is effected at 110° C. in a regenerating oil. A rotary vacuum filter separates the adduct from the mother liquor after the adduction step. Removing 3–4 percent of straight chain hydrocarbons from the oil, the pour point is lowered from 25° to 0° F. and the cloud point from 40° to 6°–8° F.

(b) The Deutsche Erdol AG Plant at Heide; (Ref: A.Hoppe "Advances in Pet. Chem and Refining, Vol. 8, Ed. Kobe-Mcketta, Interscience Pub., Newyork, 1964; A.Hoppe and H.Franz, Pet. Refiner, 36(5). 221, 1957).

The plant, with a 50 tons/day capacity, went on stream in 1954. Urea is applied to dewax gas oils and spindle oils. The process uses aqueous urea solution of high concentration and methylene chloride as an oil solvent. Mixing in the adduction step is performed by dispersing machines. Adducts are separated by filteration on a wire sieve cloth and decomposed in aqueous urea solution at 80° C.

Standard Oil Company (Indiana); (Ref: T. H. Rogers, J. S. Brown, R. Diektman and G. D. Kerns, Petrol. Refiner 36 (5), 217, 1957).

The company has operated, since 1956, a large urea dewaxing plant with a capacity of 100 tons. The process is adapted to light lubricating stocks used for low-cold-test oils. It employes a rotary filter for separating the adducts and an unspecified regeneration system.

(b) Moscow Oil Refinery (USSSR); (Ref: J. Marechal and P.De Radzitzky, J. Inst. Petroleum, 46.33–45 (1960).

The refinery has put in operation a urea dewaxing process for the production of diesel fuel of –30° to –70° F. pour point; the recovered low melting paraffins are suitable for fatty acid manufacture.

(e) Process of Shell Oil Co., Wilmington, USA; (Ref: A. Hoppe "Advances in Pet.Chem and Refining", Vol.8, Ed.Kobe-Mcketta, Interscience Pub; Newyork, 1964).

A pilot plant built in 1949 can dewax with urea hydrocarbons above the gasoline range. Adduction is carried out in urea solution and the adducts are separated by means of a rotary filter or a centrifuge or a settling tank and decomposed at 60° C. in the urea solution.

(f) Process of Shell Petroleum Co. Ltd: (Ref: A. Hoppe "Advances in Pet. Chem and Refining, Vol. 8, Ed. Kobe-Mcketta, Interscience Pub; Newyork, 1964)

This process, in principle, is the same as the preceding one. A simple settling tank accomplishes separation of the adduct. The separation procedure is termed a "Non-Filtration Process" in contrast to the filtration process. According to Goldsbrough (L. N. Goldsbrough 4 WPCP Rome, 1955, Sec.3B, Paper 6), the non-filtration process is more suitable than the filtration process for systems with paraffin or olefin content above 30%.

Decomposition of aqueous slurry is carried out at 70° C. and separation in a hot separator for ½ to 1 hour.

(g) Christex Process: (Ref: A. Hoppe, "advances in Pet. Chem. and Refining Vol. 8, Ed. Kobe-Mcketta, Interscience Pub: Newyork, 1964).

It is a semi commercial plant built in 1953, with capacity of 10 Cubic Mtr./day fcir production of n-paraffins for kerosene and gas oils. The process is mostly employed for paraffinic oils with a boiling range upto 360° C.

This process has many features in common with the processes of the Shell Oil.Co, and the Shell Petroleum Co.

It is also a non-filtration process and employs for separation purpose the so called turbulent decantation technique. The adducts are decomposed in the liquid urea solvent at 70° C. for 30 minutes.

(h) Nurex Process

Until late 1960s, no company operated a commercial plant based on urea technique for the sole purpose of extracting n-paraffins. The Nippon Mining Company of Japan claims to have installed the first unit using the Nurex Processs to extract n-paraffins in the carbon range C9 to C30. The plant has been running since the end of 1967, having a capacity of 40000 T/Yr.

The Nurex Process uses solid urea during both the adduction and adduct decomposition steps. The adduct is separated on a rotary vacuum drum filter. The decomposition is carried in an aromatic solvent for 10 min. at a temperature.<100° C. Product purity of the order of 98% and above is claimed. The outstanding features of the process can be summarised as below:

It is a solid urea process

It is suitable for processing a wide range of hydrocarbons; no process change is required to accommodate variations in feed stocks.

The feed requires no preliminary treatment such as desulphurisation.

(i) MAFKI Research Instituted Work (Ref: J.Bathory and I.Orzizag, Riv.Combust, 20(3), 140–6, 1966).

This Institute has evolved a method based on the use of solid urea to produce straight chain hydrocarbons of high purity from oil distillates. The urea crystal adduct in this method is separated by centrifuge and washed. The method is claimed to be cheaper than the Fischer-Tropsch Process.

(j) Gulf Research and Dev.Co.Process: (Ref.Carlson, Edgar et al. (Gulf R&D Co.), U.S. Pat. No. 3,433,734; CA 70, 108091g, 1969).

The above patent describes a urea proccess which can extract normal hydrocarbons in the carbon range of C6 to C54, preferably C9 to C23 from the feed stocks containing 15 to 45% by weight of n-alkane. Method of adduct decomposition is not disclosed.

(k) Other Literature References:

Way back in 1955 F. E.Mange of Petrolite Corporation reported decomposition of urea complexes by mixing the same with methanol containing water. (Chem.Specialities Mfrs.Assoc.Proc., June, 1952, 142–6). Addition compounds of urea and paraffinic hydrocarbon are decomposed by treating with 50% urea solution saturated with carbondioxide gas to yield 100% yield of paraffinic hydrocarbons (Japan 2085(54)-1954). U.S. Pat. No. 2,686,755-1954 describes decomposition of urea adduct by bringing it into contact with ammonia at a temperature ranging between 30° to 100° C. U.S. Pat. No. 2,689,845-1954 describes decomposition of urea adduct by treating it with water at 90° C. British Patent, Birt;718,703-1954, describes decomposition of decanol-urea and decanol-urea adducts by applying heat. British patent no.657,496-1951 deals with the separation of hydrocarbon mixtures reveal decomposition of adduct by heating.

According to U.S. Pat. No. 2,672,457,1954, the adduct of urea and the paraffinic hydrocarbon is fed to the top of a heated column where it is decomposed. Cooled n-pentane is fed into the bottom of this column where it cools the urea and washes it free from paraffinic hydrocarbons by a counter current flow. The cooled urea coming from the bottom of the decomposition column is suitable for reuse in the adduct formation column. Separation of hydrocarbons from the adduct has been accomplished by Phillip Petroleum Co. and described in U.S. Pat. No. 2,640,051-1953 by bringing the adduct in contact with a non reactive carrier fluid at 130°–180° F. As reported in Patent 2,879,220 elevated temperature (125°–225° F.) is used for decomposing the urea adducts. The decomposition of urea adducts has been reported by Nippon Mining Co.Ltd., Japan. (Japan 6235(58)-1958) using aqueous urea solution containing small amount of either benzene, toluene or xylene. Adduct decomposition by heating has been reported in German patent no.1,030, 492. However, to avoid the thermal decomposition of urea, the adducts are introduced in some amount of such hydrocarbons as heat carriers. U.S. Pat. No. 3,247,177 discloses separation of n-paraffins from urea adduct by decomposing it at 140° C.

Patent assigned to, M/s. Shell International (Ger. Offen. 1,914, 305–1968) reveals separation of hydrocarbon mixture using urea adduction techniques The solid adduct is decomposed with ammonia to yield the desired product. Adduct decomposition at 72° C.: using water as medium was reported in Japan 70,15,375-1970. Russian workers have reported semicontinuous process for urea deparaffination of gas oil. Decomposition of adduct was accomplished by raising the reactor temperature to 70° C. and passing in toluene. A vacuum was applied to remove the toluene from the paraffin mixture (Nefta {Zagreb}), 22(10), 801-6-1971), A. G. Ismailoy of Institute of Neftekhim.Pereraby Baku, USSR reports the decomposition of urea adduct with heat and water (Azerb.Neft.Khoz, (10),54-7, 1979). Decomposition of urea adduct either by dissolving it in methanol and/or water at 50–90° C. has reported by K. K. Bhattacharya and co-workers (Ger. Offen. DE 3, 436, 289-1984). N.Ya.Rudaklova and co-workers have reported decomposition of urea complex with water to determine the n-alkane potential in petroleum crude oil (Neft.Gazov.Prom-st.(4), 48–51,1986). Indian Patent no. 162,876 describes an improved process for selective separation of linear terminal olefinic hydrocarbons and n-paraffins from petroleum fraction using urea adduction technique.

The adduct thus formed was decomposed by stirring in hot water (80°–90° ° C.). Adduct decomposition by heating has been reported by I. D. Babaev et al. (Khim.Tekhnol.Topl.Masel, (5), 6–7, 1989.

The prior art methods discussed above have the disadvantage of poor recovery of linear hydrocarbons from the urea adduct.

Another disadvantage of the prior art methods is that hot water is generally used for separating linear hydrocarbons from the urea adduct resulting into generation of enormous amount of dilute aq. urea solution. For the recovery of solid and reusable urea from the above, lot of heat energy would be required.

Furthermore, another disadvantage of the prior art methods is that adduct is often heated to the melting point of the urea to separate linear hydrocarbons from the adduct. This leads on one hand to the thermal degradation/modification of paraffinic-olefinic hydrocarbons; on the otherhand a by-product of urea (i.e., Biuret) is formed. Biuret adversely affects both adduct formation and the degree of deparaffination (Khim.Tekhnol.Topl.Masel, 1987, (4), 22–3).

While the above are the major disadvantages of prior art methods, there are various other related disadvantages regarding the process adaptability and yield/quality of the urea as well as the linear hydrocarbons.

OBJECTS OF THE INVENTION

An object of this invention is to propose an improved process for recovery of solid and reusable urea from the urea adduction process.

Another object of this invention is to propose a process for the separation of paraffin-olefin mixture from the urea adduct in which the decomposition of adduct into urea and hydrocarbon mixture is substantial and is more than what has so far been reported.

Still a further object of this invention is to propose a process for the recovery Df solid and reusable urea in which it is possible to decompose the urea adduct at convenient temperatures and can be effectively controlled.

Yet another object of this invention is to propose a process for the recovery of solid and reusable urea by way of mechanical shearing of the adduct lattices to quantitatively separate the adduct linear hydrocarbons.

DESCRIPTION OF THE INVENTION

According to this invention there is provided a process for recovery of solid and reusable urea from the urea adduction process which comprises subjecting petroleum refinery streams to a step of urea adduction for removing unwanted branched products, aromatics and sulphur, the urea adduct thus formed being purified and dried, and then mechanically shearing the lattices of the urea 20 adduct to obtain pure and reusable urea.

In accordance with this invention the urea adduct was thoroughly washed followed by filtration and drying. The purified dry adduct was treated with organic solvent followed by mechanically shearing.

Mechanical shearing of urea lattices is carried out either by crushing, subjecting the adduct to shear between two moving surfaces or press filtering under high vacuum to recover the desired hydrocarbon. Both petroleum ether and commercial acetone are 10 used to wash the urea adduct.

The organic solvent for dispersing adduct is either petroleum ether or commercial hexane.

Apart from the presence of substantial amount of n-paraffins, secondary processes product contains high percentage of olefins. These olefins are considered and undesireable components from fuel stability point of view as they contribute to poor shelf life, glum formation, deposition, etc. on their blending into straight run products. As a way to improve the quality of distillate fuels several alternatives like hydrotreatment, hydrocracking additive treatment, etc., are being used. Efforts are also being made to convert these olefin rich streams to other useful products by processes such as addition, polymerisation, etc. In the present invention refinery streams such as Coker Kero I(CKI), Coker Ker II (CKII) gas oil and vacuum oil were utilised. However, the scope of invention is not limited to these two streams only and other paraffin-olefiri/paraffin containing feeds may be used.

High pour point of diesel is mainly attributed to the presence of long chain waxy paraffins. Removal of such components from the diesel fuel results in the improvements of its flow behaviour at low temperatures. Therefore, high pour waxy diesel fuel may also be used as a petroleum stream for the process of the present invention with an aim to reduce its pour point.

Several approaches were attempted to separate linear paraffins and olefins from the above feed. The most appropriate among them was found to be treatment of streams with urea at approximately ambient temperature to give a solid adduct which on developed mechanical shearing process gave mixture of pure linear hydrocarbons.

The following example illustrates the process for recovery of solid and reusable urea from the urea adduction process using petroleum streams as described herein. All parts or percentages are by weight and all temperatures are in degree centrigrade. unless otherwise stated. The yield of desired solid and reusable urea generated is with respect to the amount of urea used for making urea adduct at the initial stage.

EXAMPLE

In the urea adduction process, 16 kg. of petroleum stream was charged in 1275 liter reactor fitted with condenser, efficient stirring, solid and liquid addition devices and heating/cooling system, 28 kg. of commercial urea (product tested by X-Ray Diffraction Technique) was then added followed by 24 kg. alcohol and 11.5 kg. petroleum ether. The contents were agitated at 20°–40° C. for 4–8 hours. The urea adduct was then separated and washed thoroughly with petroleum ether. The adduct was then dried at 60°–80° C. for 2–4 hours. The dried adduct was treated with 2–5 kg. of petroleum ether for making flowable slurry. This adduct slurry was subjected to mechanical shearing at various load conditions and for a given period of time 24.6 kg. (88%) of pure and reusable urea was obtained. This urea sample was thoroughly characterised by XRD technique and found to be identical with that of the initial urea used for the process. 3.2 kg. of solid and reusable urea was obtained from the filterate after the removal of solvents and subjecting the recovered solid product to the mechanical shearing as herein described.

The solid urea thus obtained was reused in subsequent urea adduction process with same efficiency as that of the original urea used for the initial urea adduction process.

We claim:

1. A process for recovery of solid and reusable urea from the urea adduction process which comprises subjecting petroleum refinery streams to a step of urea adduction for removing unwanted branched products, aromatics and sulphur, the urea adduct thus formed being purified and dried and then mechanically shearing the lattices of the urea adduct to obtain pure and reusable urea.

2. A process as claimed in claim 1. wherein the mechanical shearing of urea lattices is carried out by crushing.

3. A process as claimed in claim 1 wherein the mechanical shearing is carried out by subjecting the adduct to shear between two moving surfaces.

4. A process as claimed in claim 1 wherein the mechanical shearing is carried out by press filtering under high vacuum to recover the desired hydrocarbons.

5. A process as claimed in claim 1 wherein both petroleum ether and commercial acetone are used to wash the urea adduct.

6. A process as claimed in claim 1 wherein organic solvent for dispersing adduct is selected from petroleum ether and commercial hexane.

7. A process as claimed in claim 1 wherein regenerated solid urea is recycled.

8. A process as claimed in claim 1 wherein recovered solvents are recycled.

* * * * *